(12) United States Patent
Bertsch

(10) Patent No.: US 10,216,150 B2
(45) Date of Patent: Feb. 26, 2019

(54) APPARATUS FOR ATOMIC CLOCK, ITS OPERATING METHOD AND ITS MANUFACTURING METHOD

(71) Applicant: MEMSCAP, Crolles (FR)

(72) Inventor: Nicolas Bertsch, Saint Jean le Vieux (FR)

(73) Assignee: MEMSCAP, Crolles (FR)

( * ) Notice: Subject to any disclaimer, the term of this patent is extended or adjusted under 35 U.S.C. 154(b) by 175 days.

(21) Appl. No.: 15/200,410

(22) Filed: Jul. 1, 2016

(65) Prior Publication Data

US 2017/0003658 A1 Jan. 5, 2017

(30) Foreign Application Priority Data

Jul. 3, 2015 (EP) ..................... 15175309

(51) Int. Cl.
*H03L 7/26* (2006.01)
*G04F 5/14* (2006.01)
*G01N 24/10* (2006.01)
*G01R 33/30* (2006.01)
*G01R 33/60* (2006.01)
*G01R 33/383* (2006.01)

(52) U.S. Cl.
CPC ............ *G04F 5/14* (2013.01); *G01N 24/10* (2013.01); *G01R 33/302* (2013.01); *G01R 33/60* (2013.01); *H03L 7/26* (2013.01); *G01R 33/383* (2013.01)

(58) Field of Classification Search
CPC ..... G01R 33/302; H03L 7/26; G01C 19/5769; G04F 5/14
USPC .............. 331/3, 94.1; 324/309, 319
See application file for complete search history.

(56) References Cited

U.S. PATENT DOCUMENTS

| 7,142,066 B1 | 11/2006 | Hannah et al. |
| 2008/0164874 A1 | 7/2008 | White et al. |
| 2012/0074818 A1* | 3/2012 | Crowley ............ G01C 19/5769 310/348 |

(Continued)

FOREIGN PATENT DOCUMENTS

WO   WO-2008091364 A2   7/2008

OTHER PUBLICATIONS

European Search Report issued in Application No. EP 15175309 dated Jan. 13, 2016.

*Primary Examiner* — Arnold Kinkead
(74) *Attorney, Agent, or Firm* — Marshall, Gerstein & Borun LLP

(57) ABSTRACT

An apparatus for an atomic clock includes first and second distinctive substrates, each having at least a planar surface substantially parallel therebetween. The apparatus also includes a medium having particles capable of undergoing energetic transition between at least two energy levels, said medium being located in the space defined between the planar surfaces. It further includes a magnetic device arranged to the first substrate and generating at least in the volume of the medium a predetermined static magnetic field B the direction of which is substantially parallel or perpendicular to the planar surfaces and an excitation device arranged to the second substrate and generating an excitation magnetic field H at, at least an excitation frequency, the direction of said excitation magnetic field H in the volume of the medium being substantially orthogonal to said direction of the static magnetic field B.

19 Claims, 7 Drawing Sheets

(56) References Cited

U.S. PATENT DOCUMENTS

| | | | |
|---|---|---|---|
| 2013/0229179 A1* | 9/2013 | Lee | G01N 24/08 324/309 |
| 2014/0225678 A1* | 8/2014 | Yano | G01R 33/26 331/94.1 |
| 2016/0349283 A1* | 12/2016 | Bramhavar | G01P 15/097 |

* cited by examiner

APPARATUS FOR ATOMIC CLOCK, ITS OPERATING METHOD AND ITS MANUFACTURING METHOD

CROSS-REFERENCE TO RELATED APPLICATIONS

This application claims the benefit of priority under 35 U.S.C. § 119 of prior-filed European Patent Application No. 15175309.2, filed Jul. 3, 2015, the entire content of which is hereby incorporated herein by reference, in its entirety and for all purposes.

TECHNOLOGICAL FIELD

The present disclosure is in the general field of electron spin resonance detection. More precisely, it relates to spin resonance detection device for the realization of miniature atomic clocks, its operating method and its manufacturing method.

BACKGROUND

Spin resonance spectroscopy (ESR) or Electron paramagnetic resonance (EPR) is a widely used technique for studying and characterizing materials with unpaired electrons. The technique depends on the fact that certain atomic systems have a permanent magnetic moment. The energy levels of the magnetic system are influenced by the surrounding atoms and by external magnetic fields.

Every electron has a magnetic moment and spin quantum number $s=½$, with magnetic components $m_s=+½$ and $m_s=-½$. In the presence of an external magnetic field with strength $B_0$, the electron's magnetic moment aligns itself either parallel or antiparallel ($m_s=-½$ or $m_s=+½$ respectively) to the field, each alignment having a specific energy due to the Zeeman effect. Therefore, the splitting of the energy levels between the lower and the upper state of energy $\Delta E$ is directly proportional to the magnetic field's strength. An unpaired electron can move between the two energy levels by either absorbing or emitting a photon of energy $h\nu$ such that the resonance condition, $h\nu=\Delta E$, is obeyed. This leads to the fundamental equation of ESR (or EPR) spectroscopy: $h\nu=g_e*\mu_B*B_0$, where $g_e$ is the electron's so-called g-factor, $\mu_B$ is the Bohr magneton and $B_0$ is the external magnetic field applied to the material.

Once the energy levels of a system have been found, one needs to find an appropriate manner to detect them.

A first detection approach is the consideration of the absorption of electromagnetic radiation due to transitions between levels. This absorption will occur when $h\nu=\Delta E$. In the case of magnetic phenomena, energy absorption occurs in response to an alternating magnetic field of the radiation. Generally, a main external magnetic field $B_0$ is produced by an electromagnet, controlled by a power supply controller which allows the magnetic field to be ramped slowly up or down. A microwave generator and resonant cavity are used to provide a time-varying magnetic field H. A lock-in amplifier is used to detect the reduction in microwave power produced by the ESR/EPR absorption. In addition, the required alternating magnetic field H is generally produced by a solid state oscillator operating in general in the GHz range. The oscillator is coupled to the resonant cavity containing the sample which is exposed to microwaves at a fixed frequency. By increasing the external magnetic field $B_0$, the gap between the $m_s=+½$ and $m_s=-½$ energy states is widened until it matches the energy of the microwaves. At this point the unpaired electrons can move between their two spin states. Since there are typically more electrons in the lower state, due to the Maxwell-Boltzmann distribution, there is a net absorption of energy, and it is this absorption that is monitored and converted into a spectrum. When the oscillator frequency matches the cavity frequency, the amplitude of the magnetic field H is increased relative to the oscillator amplitude by the Q-factor of the cavity. Since Q is in the range of a few thousands, this substantially enhances the field intensity and hence the absorption by the sample. Some of the power entering the cavity is allowed to leak out the opposite side. The amount of leakage is determined by the input power and by sample absorption. The output power falls on a diode which converts it to a near-DC. This voltage, proportional to the transmission through the cavity, constitutes the output signal.

A second detection approach is the use of the basic concept which is analogous of nuclear magnetic resonance (NMR), but it is electron spins that are excited instead of the spins of atomic nuclei. The principle of this detection method involves two sequential steps:

i) the alignment (or polarization) of the spins in an applied and constant magnetic field $B_0$, and ii) the perturbation of this alignment of the spins by employing an electro-magnetic signal H varying with time (usually in radio frequency range).

As shown in the ESR equation above, the required perturbing frequency of H is dependent upon the static magnetic field $B_0$ and the spins of the material of observation. Theoretically, the two fields are to be perpendicular to each other to maximize the ESR signal strength. Resonant absorption by spins will occur only when electromagnetic radiation of the correct frequency (e.g., equaling the Larmor precession rate) is being applied to match the energy difference between the spin levels in a constant magnetic field $B_0$ of the appropriate strength.

Recently, proposals regarding the exploitation of ESR property of endohedral fullerenes in a solid state atomic clock have been made. Such atomic clocks plan to combine the sharp resonance of ESR of endohedral fullerenes and their small size to create high stability frequency and timekeeping standards thanks to the sharp linewidth of the split of the energy levels of the material used.

For example, such atomic clock using endohedral fullerenes is described in document U.S. Pat. No. 7,142,066. However, the alignment device described in this document is not optimal since it creates spatial variations of the value and of the direction of the magnetic field $B_0$ over the spatial range of the solid layer, due notably to the so-called "corner effects" of the magnetic field generated by the alignment device. In other words, the corner effects induced a non-homogenous magnetic field in the spatial range of the solid stated used. As the above equation of ESR shows, the excitation frequency at which ESR/EPR occurs exhibits a strong dependency towards the value of the applied external magnetic field $B_0$. Thus, such gradient of the magnetic field value creates larger absorption spectra of the particles and therefore an output clock signal that exhibits an increased linewidth.

In addition, in this document U.S. Pat. No. 7,142,066, the excitation is created within the plane of the substrate by a varying magnetic field H generated by two capacitors. As mentioned earlier, maximum signal at resonance occurs when excitation magnetic field H is orthogonal to the fixed magnetic field B. Hence the variation of the direction of the magnetic field would translate into a lower useful signal as only the particles having their spin perpendicular to the field generated by the excitation device would contribute to the output signal.

Moreover, in this document U.S. Pat. No. 7,142,066, the sensitivity of the device to external fields (like any electro-magnetic field present in a mobile handset), which can also strongly affect the device performance, is not addressed. Practical manufacturing of the device described in this document is also not optimized. The ability to deposit magnetic material on top of a semiconductor wafers (or die) is limited by the thermal budget of the underlying electronics and materials. Typical sputtering of magnetic material requires high temperature (between 500° C. and 650° C.) processing to obtain magnetic properties practically useful. At such temperatures, the underlying electronics and transistors are affected.

In order to alleviate some of the above identified problems, document U.S. Pat. No. 8,217,724 recommends a device in which the medium must be a specific material for which two particular energy levels have an energy difference that is, to first order, independent of the magnetic field intensity over a certain range.

In addition, it recommends the use of micro-coils as a magnetic device to apply an adjustable magnetic field to the medium. However, in order to generate the required biasing field $B_0$, some current needs to flow constantly in the micro-coils during the device operation which makes this solution incompatible with most recent mobile handsets power consumption requirements.

Moreover, the excitation is performed using a microwave and output signal is then generated using a feedback control loop based on the detection of absorption of the exciting electro-magnetic wave. However, the energy level of the transition requires excitation at a few tens of Mega Hertz which requires resonant cavities and waveguides in the millimeter range. Such dimensions are completely incompatible with miniaturization and costs requirements, notably in the industry of mobile handsets and Internet of Things (IOT).

Another drawback of the solution described in this document is the complexity of operating the device and the number of elements which need to be combined to operate. As an example, operating the device starts with locking the magnetic field to a certain value using a field stabilization circuit and feedback loop system based on absorption of electromagnetic wave. Such operation typically requires unnecessary complexity in the electronics circuitry.

SUMMARY OF THE DISCLOSURE

Therefore, there is a need for a less complex and more efficient solution that allows the realization of a miniature atomic clock.

Thus, the disclosed embodiments aim at providing a solution that improves the uniformity of the applied magnetic field over a large spatial range and notably over a medium capable of undergoing energetic transitions between at least two energy levels, to thereby reducing the linewidth of the output signal and improving frequency stability and time-keeping properties of the atomic clock.

The disclosed embodiments also aim at providing a detection device for atomic clock having reduced sensitivity to external or environmental conditions.

Another aim of the disclosed embodiments is to provide a miniature atomic clock having low cost manufacturing process, low cost packaging, and low power consumption in operating mode.

Yet another aim of the disclosed embodiments is to provide a solution having increased signal output by use of a design poorly sensitive to in-plane variations or out-of-plane variations of the direction of the applied external magnetic field.

Another aim of the disclosed embodiments is to provide a miniature atomic clock having simplified operation by the use of simplified design including, but not restricted to, the magnet device, the excitation device and detection device.

A further aim of the disclosed embodiments is to provide a miniature atomic clock having a manufacturing process compatible with conventional processes such as MEMS (acronym for "Micro-electromechanical System"), IC (acronym for "Integrated Circuit") or semiconductor manufacturing processes.

Another aim of the disclosed embodiments is to provide a miniature atomic clock having a self-stabilized output signal.

For these purposes, an object of the disclosed embodiments is an apparatus for atomic clock comprising:
first and second distinctive substrates, each having at least a planar surface substantially parallel therebetween;
a medium having particles capable of undergoing energetic transition between at least two energy levels, said medium being located in the space defined between said planar surfaces;
a magnetic device arranged to the planar surface of the first substrate and generating at least in the volume of the medium a predetermined static magnetic field B the direction of which is substantially parallel to a reference plane parallel or perpendicular to the planar surfaces;
an excitation device arranged to the second substrate and facing the medium, said excitation device generating an excitation magnetic field H at, at least an excitation frequency, the direction of said excitation magnetic field H in the volume of the medium being substantially orthogonal to said direction of the static magnetic field B.

In other words, the magnetic device used in the presently disclosed embodiments is chosen so as to produce a uniform or quasi-uniform magnetic field at least over the entire volume of the medium, and preferably without the need of any electrical current. The uniformity or quasi-uniformity of the static magnetic field over at least the volume of the medium is notably reflected in the fact that the intensity and/or the direction of the magnetic field are constant or present an insignificant variation. Besides, in order to avoid any corner effect, the dimensions of the magnetic device should be preferably larger than that of the medium. Of course, the limit of the acceptable uniformity in the entire volume of the medium will notably depend on the design of the magnetic device and of the medium. For instance, such uniformity can be obtained by adapting the volume of the medium to that of the magnetic device by using for example the mapping of the magnetic field created by the magnetic device.

In addition, the magnetic device and the excitation device are both fixed to distinctive substrates with planar surfaces as reference surfaces. By setting the direction of the magnetic field and the excitation magnetic field according to the planar surface during the manufacturing process, and by sealing the two substrates so that the planar surfaces remain substantially parallel to each other, one can ensure that the static magnetic field remains substantially orthogonal to the excitation magnetic field during the operation. This arrangement is an advantage for generating a maximum signal at resonance and for miniaturization and simplification of the manufacturing process.

In practice, this can be achieved by using a structure of permanent magnet as the magnetic device.

According to a variant, the structure of permanent magnet can be a single permanent magnet or a plurality of distinctive permanent magnets.

According to another variant, the structure of permanent magnet can also be a portion of the first substrate, for example by processing the first substrate.

The magnetic device can be located on the planar surface of the first substrate or can be located in a cavity of the first substrate.

Of course, the location of the medium in relation to the magnetic device will depend on the design and on the magnetization of the permanent magnet and thus on the mapping of the magnetic field created by the structure of permanent magnet. Advantageously, the location of the magnetic device and the medium is such that medium sees a homogeneous magnetic field without any corner effect. For example, the magnetic device can be placed facing and at distance from the medium or can be fixed to the first substrate.

As for the excitation device, it is entirely fixed to the second substrate, for example, integrated in the thickness of the second substrate.

According to an embodiment, it is also possible to add any components so as to detect the frequency at which the resonance occurred in the medium and to set the excitation frequency of the excitation device accordingly. Moreover, the excitation device may be designed to work as an excitation magnetic field generator and also to contribute to the detection of the spin resonance through the monitoring of, for example, one of its electrical characteristics that may vary when a spin resonance occurs in the medium. Of course, the detection device performing such monitoring can also be fixed to the second substrate together with the excitation device.

Thus, according to an embodiment, the apparatus may also comprise:
  a frequency generator generating a tunable frequency, said excitation frequency being based on said tunable frequency;
  a detection device detecting the occurrence of a spin resonance of the medium by monitoring a signal representative of the influence of the energetic transition of the particles over the excitation device; and
  a frequency-lock device locking the generated tunable frequency to the frequency at which the spin resonance has occurred.

In a variant, the excitation device can be formed with a structure of planar micro-coil to generate the excitation magnetic field H, at one or multiple excitations frequencies. Said structure of planar micro-coil may comprise at least a spiral planar micro-coil or at least a spiral multilayers micro-coil. In practice, one can use two or multiple microcoils to increase the signal intensity or make signal treatment to increase the clock accuracy.

In this case, the detection of the spin-resonance may be achieved by detecting, without measuring, a peak in a signal representative of the influence of the spin-resonance over the excitation device.

According to an embodiment, the detection device may be a module detecting a variation of the electrical impedance of the structure of planar micro-coil for detecting the occurrence of a spin resonance of the medium.

According to another embodiment, the detection device may be a module detecting a variation of the current intensity of the structure of planar micro-coil for detecting the occurrence of a spin resonance of the medium.

According to another embodiment, the detection device may be a module detecting a variation of the voltage value between the ports of the planar micro-coil for detecting the occurrence of a spin resonance of the medium.

In order to determine and to lock the excitation frequency to the frequency at which the spin resonance occurs in the medium, frequency generator and frequency-lock device are used. The frequency generator is notably designed to work for adjusting the excitation frequency whereas the frequency-lock device is designed to work for locking the excitation frequency at which the spin resonance has occurred. Of course, the frequency generator and/or the frequency-lock device may be fixed to the second substrate. However, they could also be integrated in a stand-alone component(s) like Integrated Circuit(s)).

In practice, the tunable frequency can be generated by a frequency synthesizer, such as a Voltage Controlled Oscillator (VCO) which can be coupled with at least one frequency divider and/or a multiplier.

As for the frequency-lock device, it can be a Phase Lock Loops (PLL) designs type.

Advantageously, in order to improve the signal to noise ratio, the apparatus for atomic clock may further comprise an oscillating magnetic device generating an oscillating magnetic field H' substantially parallel to the static magnetic field B. In practice, said oscillating magnetic field is added (super-imposed) to the static magnetic field in the medium, introducing small amplitude magnetic field modulation. The modulation amplitude is normally less than the linewidth of the resonant curve of the medium. The modulation frequency is normally lower than the frequency at which the Electron Spin Resonance of the medium occurs.

Said oscillating magnetic device can also be integrated in the second substrate.

Advantageously, the apparatus for atomic clock may further comprise an isolating layer between the medium and the excitation device.

Advantageously, the apparatus may be covered by a patterned metal electro-magnetic shield in order to reduce the sensitivity of the apparatus to external environment.

In practice, in order to avoid any stress due to temperature variation of the medium, the apparatus may further comprise device for maintaining the volume in which the medium is located at a substantially constant temperature.

Another object of the presently described embodiments is a method for manufacturing the apparatus for atomic clock described above. The method comprises:
  forming a magnetic device fixed to a first substrate having at least a planar surface, the magnetic device generating a predetermined static magnetic field B the direction of which is substantially parallel to a reference plane parallel or perpendicular to the planar surface of the first substrate;
  forming at least an excitation device in a second substrate having at least a planar surface, said excitation device generating an excitation magnetic field H having a direction substantially orthogonal to said reference plane;
  forming a medium having particles capable of undergoing energetic transition between at least two energy levels on one of the first and second substrates;

sealing the first substrate to the second substrates so that their respective planar surfaces are facing each other and substantially parallel therebetween.

The manufacturing method may further comprise:
coupling the detection device described above to the excitation device;
coupling the frequency generator described above to the excitation device; and
coupling the frequency-lock device to the detection device and to the frequency generator.

Another object of the disclosed embodiments is a method for operating the apparatus for atomic clock described above. The operating method comprises:
simultaneously driving a frequency generator to sweep a tunable frequency applied to the excitation device within a predetermined range of frequencies, and monitoring the excitation device to detect the occurrence of a spin resonance in the medium;
when a spin resonance is detected, driving the frequency generator to lock said tunable frequency to the frequency at which the spin resonance has occurs;
setting the excitation frequency to said locked tunable frequency.

The operating method may also comprise, continuously monitoring the excitation device so as to stabilize the tunable frequency to said frequency at which the spin resonance has occurs.

In practice, the operating method may also comprise, stabilizing the temperature of the volume in which the medium is located at a substantially constant temperature.

BRIEF DESCRIPTION OF THE DRAWINGS

Other features and advantages will appear more clearly from the description of embodiment made hereinafter, as an indication and by no means restrictive, with reference to the accompanying drawings, wherein.

Figure 1:
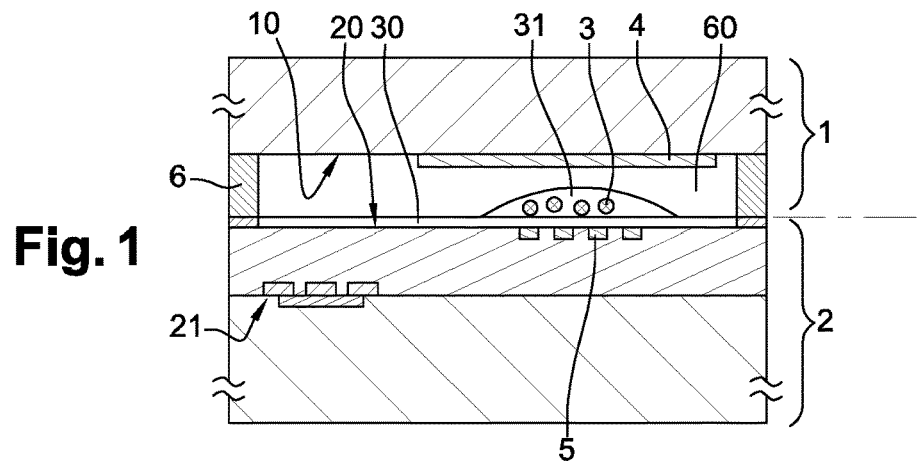
FIG. 1 is a schematic cross-section view of the apparatus according to a particular embodiment.

In accordance with common practice, the various described features are not drawn to scale but are drawn to emphasize specific features relevant to the exemplary embodiments.

DETAILED DESCRIPTION

The apparatus for atomic clock according to a particular embodiment comprises notably:
two distinctive substrates 1, 2;
a medium 3 capable of undergoing energetic transitions between at least two energy levels;
a magnetic device 4, such as a structure of permanent magnet, to produce a predetermined static magnetic field B;
an excitation device 5, such as a structure of spiral micro-coils, to generate an excitation magnetic field H orthogonal to the static magnetic field B and to detect the occurrence of spin resonance of the medium;
a frequency generator 54 generating a tunable frequency to be applied to the excitation device;
a detection device 52 monitoring the excitation device in order to detect the occurrence of a spin resonance of the medium;
a frequency-lock device 53 for locking the generated tunable frequency to the frequency at which the spin resonance has occurred.

According to particular embodiments illustrated in FIGS. 1 to 4, the first substrate 1, also called "the magnetic substrate", and the second substrate 2 also called "the reference substrate", have both a planar surface 10, 20. The first and the second substrates 1, 2 are sealed together via a mechanical connection 6 so that the planar surfaces 10, 20 are facing and parallel to each other. Thus, the first and second substrates 1, 2 form a stack in which the planar surfaces 10, 20 and the mechanical connection 6 define a space 60 inside which the medium 3 is located.

The magnetic device 4 is affixed to the planar surface 10 of the first substrate 1 or located in a recess 12 of the first substrate 1. The excitation device 5 is fixed to the planar surface of the second substrate 2, preferably in the thickness of the second substrate 2.

Figure 2:
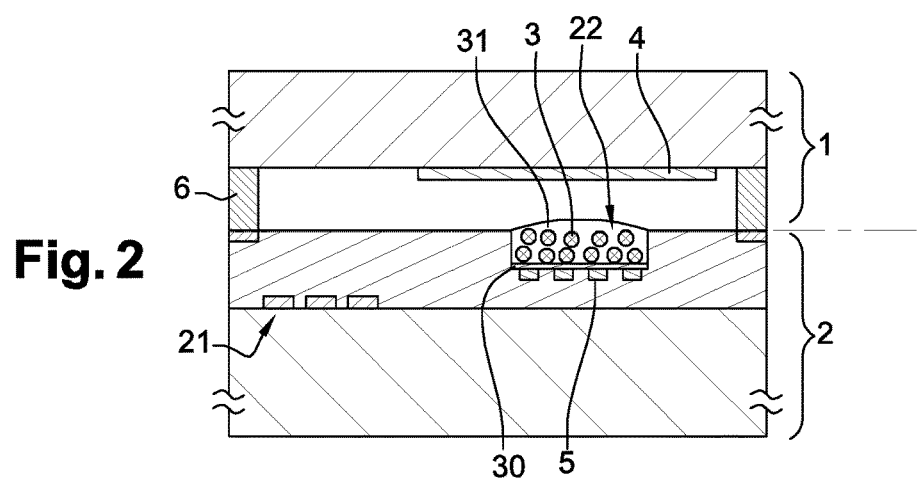
FIG. 2 is a schematic cross-section view of the apparatus according to another embodiment wherein the medium is located in a recess of the reference substrate.

The medium 3 is placed between the magnetic device 4 and the excitation device 5. The medium 3 may be directly affixed on the planar surface 20 of the second substrate 2 (FIGS. 3 and 4), or may be separated from the excitation device 5 by an isolating layer 30 to electrically isolate the medium 3 from the excitation device 5 (FIGS. 1 and 2). The medium may also be located in a recess 22 of the second substrate 2 as illustrated in FIGS. 2 and 4. In addition, the medium 3 may be spatially constrained on top of the planar substrate 20 of the second substrate 2 or on top of the isolating layer 30 via cover layer 31.

Oscillation magnetic device 7a, 7b can be provided in the thickness of the second substrate 2 to generate an oscillating magnetic field H' to be super-imposed to the static magnetic field B, so as to improve signal to noise ratio.

Active areas 21 may also be provided in the second substrate 2. Such active areas 21 may include regions that will make mechanical and/or electrical contact with the first substrate 1, as well as circuitry for driving the excitation device such as the frequency device 54 and the frequency-lock device 53, and circuitry for sensing output signals from the excitation device 5 such as the detection device 52. Such circuit could be made with another chip or may be made with conventional Silicon (Bi)CMOS circuitry/technology.

The general operation mode of the apparatus is the following: when the medium 3 is exposed to the static magnetic field B generated by the magnetic device 4, without further excitation, the split of energy states in the medium 3 occurs as described above. The excitation device 5 is in a given and stable state. Superposing now an excitation magnetic field H perpendicular to the static magnetic field B, thanks to the excitation device 5, and oscillating at a frequency so that the energy of the electromagnetic wave matches the difference of energy between at least two energy states of the medium 3 (the resonant frequency of the medium), spin-resonance occurs and the state of the excitation device is modified. With appropriate lock-in circuitry and feedback control loop based on the state of the excitation device 5, the excitation frequency of the excitation device 5 can be locked to the resonant frequency of the medium. The system is then self-controlled and stabilized. The output of the miniature atomic clock can then be a signal which frequency can be set to any multiple of the resonant frequency of the medium.

The mechanical and geometrical configurations of the elements of the apparatus will be now described, followed by examples of its operating method and its fabrication process.

The Medium

The medium 3 includes spatially constrained substantially isolated particles exhibiting energy transitions or electronics oscillations such as, hyperfine transitions, which can be detected or used to keep track of time either directly or indirectly.

Without limiting the scope of the following claims, the particles may be included within endohedral fullerenes such as, for example, buckyballs, or may be made of endohedral fullerenes. For example, the medium 3 may be a solid layer including substantially isolated particles or endohedral fullerenes in solid diluent or coated endohedral fullerenes as described in the document U.S. Pat. No. 7,142,066 B1 from column 3 lines 20 to column 8 lines 34. The medium 3 may also be made of material such as described in the document U.S. Pat. No. 8,217,724 B1 from column 3 lines 10 to column 4 lines 28.

The Magnetic Device

The magnetic device 4 is preferably a structure of permanent magnet designed and located in relation to the medium 3, so as to generate a predetermined uniform or quasi-uniform static magnetic field B over at least the volume of the medium 3. The use of permanent magnets enables powerless biasing of the medium with constant, quasi-homogeneous magnetic field over the full volume occupied by the medium. Such powerless biasing is critical to achieve ultra-low power operation of the atomic clock in mobile handsets for instance.

The homogeneity of the magnetic field over the medium may be obtained by designing the The uniformity or quasi-uniformity of the static magnetic field over at least the volume of the medium is notably reflected in the fact that the intensity and the direction of the magnetic field are constant or present an insignificant variation.

Figure 13:
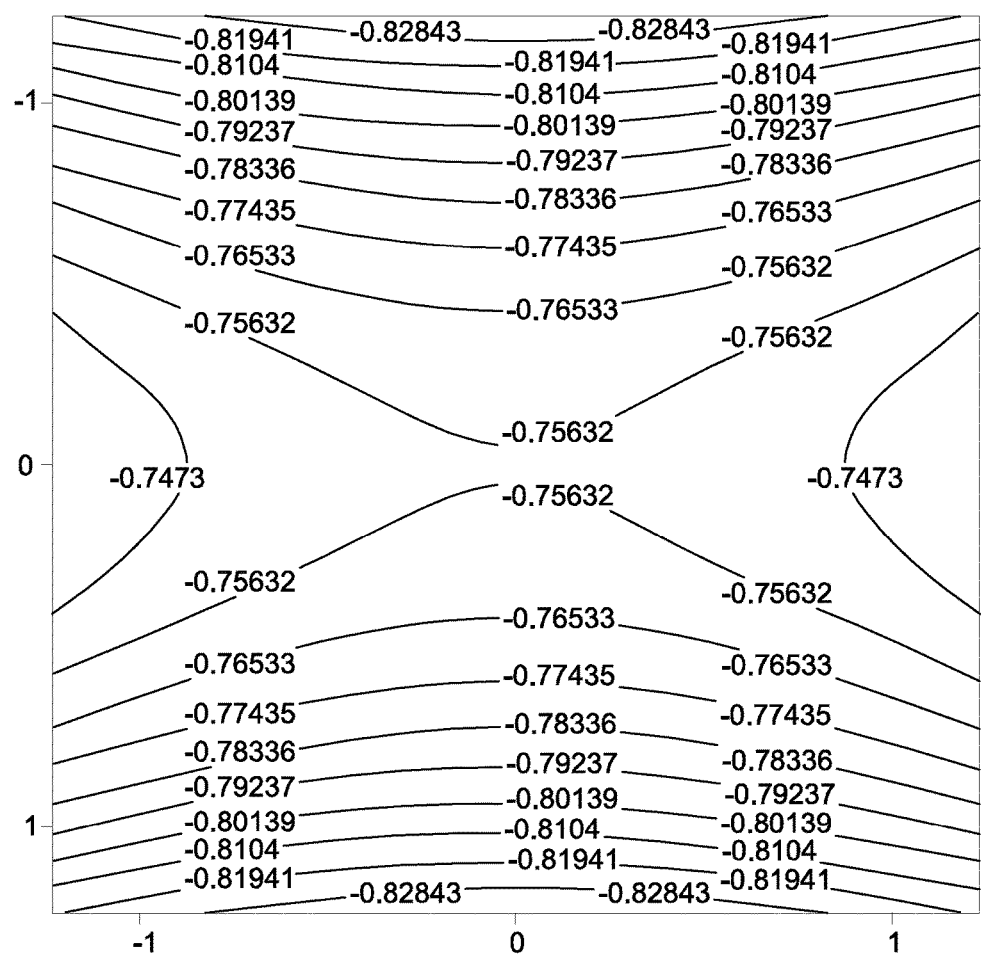
FIG. 13 shows schematically a portion of a mapping of the magnetic field created by a permanent magnet over the medium in a plane parallel to the planar surface of the substrate.

For example and without limiting the scope of the following claims to this particular example, FIG. 13 illustrates a possible homogeneity of the static magnetic field lines in a medium within a plane parallel to the planar surface of the second substrate, according to a particular embodiment. The distribution of the magnetic field intensity illustrated in FIG. 13 is generated with the area occupied by the magnetic device on the planar surface of 1 mm×1 mm over a 250 µm×250 µm area of the medium. In this particular embodiment, the permanent magnet is formed in a substrate by sputtering, the medium is of nitrogen endohedral fullerene N@$C_{60}$, and the distance between the permanent magnet and the medium is about 2 µm.

Figure 3:
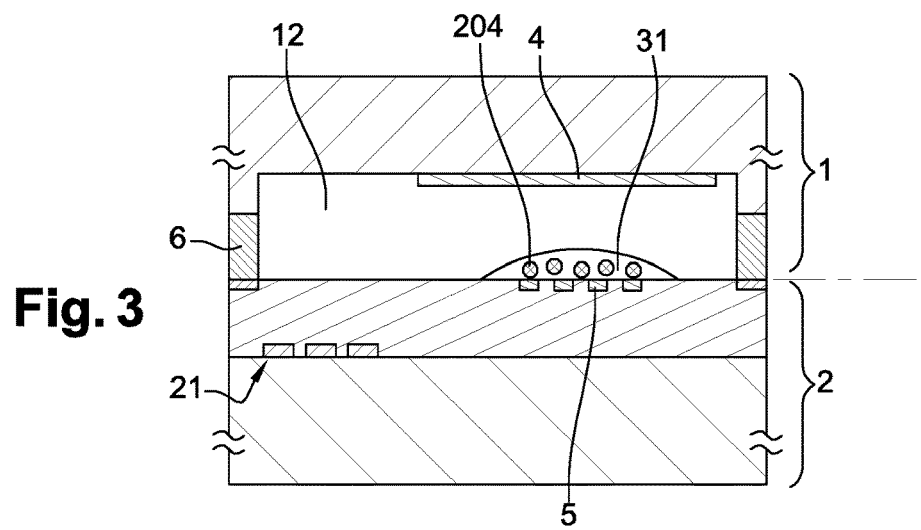
FIG. 3 is a schematic cross-section view of the apparatus according to another embodiment wherein the magnetic device is located in a recess of the magnetic substrate.
Figure 4:
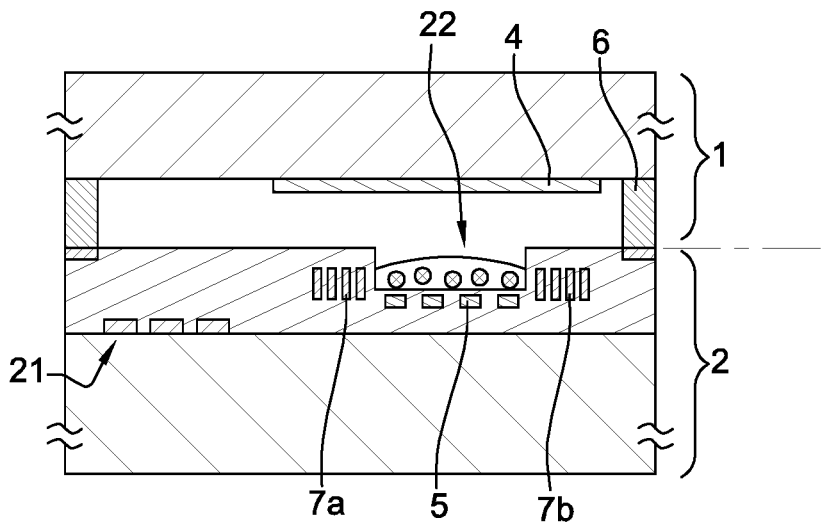
FIG. 4 is a schematic cross-section view of the apparatus according to another embodiment wherein the apparatus comprises an oscillating magnetic device for modulating the static magnetic field.

As shows in FIG. 3, the gradient of the magnetic field intensity over the volume of the medium is varying from 0.75 mT to 0.83 mT. This represents less than 10 mT variation over the area of the medium and a gradient less than 1 micro Tesla per micro micrometer. Of course, there are multiple aspects of the design of the clock affecting the distribution of the magnetic field over the medium including (and without restriction) the presence of mumetals in the vicinity of the clock.

In a variant, the magnetization of the structure of permanent magnet can be set such that the direction of the static magnetic field B in the volume of the medium 3 is substantially parallel to the planar surface 10 of the first substrate 1. This variant corresponds to the embodiment in which the static magnetic field is set in-plane and the excitation magnetic field is set out-of-plane.

In another variant, the magnetization of the structure of permanent magnet can be set such that the direction of the static magnetic field B in the volume of the medium 3 is substantially orthogonal to the planar surface 10 of the first substrate 1. This variant corresponds to the embodiment in which the static magnetic field is set out-of-plane and the excitation magnetic field is set in-plane. In such configuration, the excitation device should be designed to generate an excitation magnetic field H parallel to the planar surface in order to maintain the orthogonality of the two magnetic fields within the volume occupied by the medium.

The magnetic device may be made of a single permanent magnet. Besides, the dimensions of the permanent magnet is such that the area occupied by the permanent magnet according to the planar surface 10 of the first substrate 1 should preferably expands beyond the area occupied by the medium 3. As such, corner effects of the permanent magnet can be avoided and non-uniformity of the magnetic field over the medium is minimized.

Figure 5:
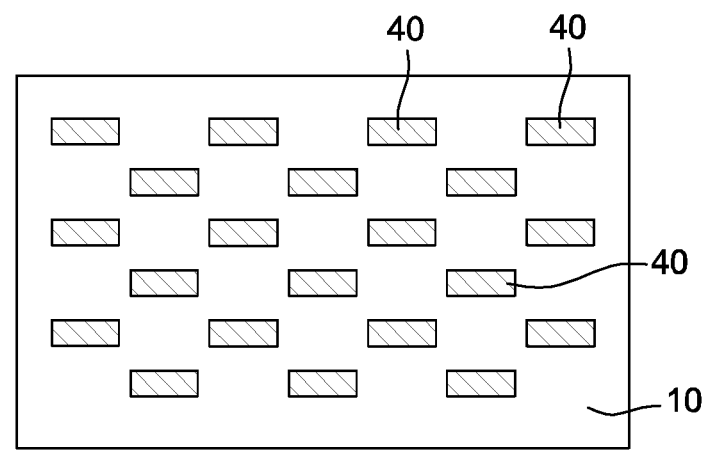
FIG. 5 is a schematic plan view of a simple pattern of independent permanent magnets used as the magnet device according to another embodiment.

The magnetic device may also be formed with a plurality of distinctive permanent magnets. The plurality of permanent magnets should be arranged in a pattern such that the static magnetic field is considered homogeneous over the thickness of the medium 3. For example, FIG. 5 shows a simple pattern of small film of permanent magnets 40 which could be used in an embodiment. The space between the magnets 40 and the patterns of the magnets depend on the magnets material properties. Advantageously, the area occupied by the distribution of the magnets 40 extends beyond the physical dimensions of the space occupied by the medium in order to avoid corner effects.

Setting the Appropriate Distance Between the Magnet Device and the Medium

The location of the permanent magnet and the medium should be such that the gradient of the magnetic field over the thickness of the medium can be neglected.

For example, the static magnetic field B can be generated using thin film magnet(s) affixed on the planar surface 10 of the first substrate 1. For such film magnets, which are much thinner than wider, close by the magnet, the stray field is strongest at the edge of the magnet, and drops off quickly as we move out from the edge. That is to say, such film magnets exhibit strong gradient of the stray fields in their vicinity but such gradient fades out after a few hundreds of nanometer of distance and the magnetic field becomes quasi-homogeneous over a large area and depth.

In practice, the cartography of the magnetic field lines created by the chosen magnetic device can be used to estimate the location of the magnetic device relative to the medium.

For example, the medium can be placed facing and at distance of the magnetic device. An appropriate distance between the medium and the magnetic device can be obtained by adjusting the thickness of the mechanical connection 6. However, as the thickness of the mechanical connection 6 is usually linked to established manufacturing processes and limited to a maximum of a few microns, the manufacturing process design rules may not allow the necessary tuning/modification of this thickness. As such, the distance between the magnetic device and the medium can be tuned using other approaches. For example, the desired distance between the magnetic device and the medium can be set by placing the magnetic device 4 in a recess 12 of the first substrate 1, or by placing the medium 3 in a recess 22 of the second substrate 2, or by combining any of these solutions. Homogeneous depth of the recess across the substrate can be further improved using for example Silicon On Insulator substrates for which the insulating layer is used as an etch stop of the recess and the thickness of the Silicon layer on top of the insulating layer is very well controlled by the manufacturer of the SOI substrates.

The Excitation Device

In the present solution, the excitation device is designed to generate the excitation magnetic field H and to be used as a sensor for the detection of the spin resonance.

Figure 6A:
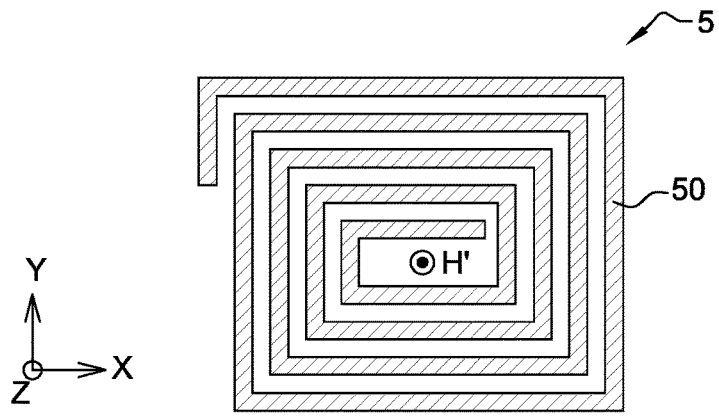
FIG. 6A is a schematic plan view of a planar micro-coil as the excitation device according to an embodiment.

In one embodiment, the excitation device is a planar spiral micro-coil 50 as shown in FIG. 6a.

A high frequency current passing through the coil generates a high frequency electromagnetic field. Over a certain distance away from the coil and certain spatial range (notably in the proximity of the last conductive layer of the micro-coil), such high frequency magnetic field is perpendicular to the plane (x,y) formed by the planar micro-coil and can be used as the excitation magnetic field H. By positioning the micro-coils properly in the second substrate 2, the high frequency electromagnetic field created can be orthogonal to the static magnetic field over the medium.

Besides, by changing the intensity of the current flowing through the micro-coil, the magnitude of the exciting magnetic field can be changed, and by changing the frequency of the current flowing through the micro-coil, the frequency of the exciting magnetic field can also be changed. Electron Spin Resonance or Spin Resonance is a resonant mechanism. This implies that, whenever the excitation frequency is set to the resonant frequency of the spins of the medium, the spins react abruptly and the excitation is made even at low magnitude of the magnetic field.

Figure 6B:
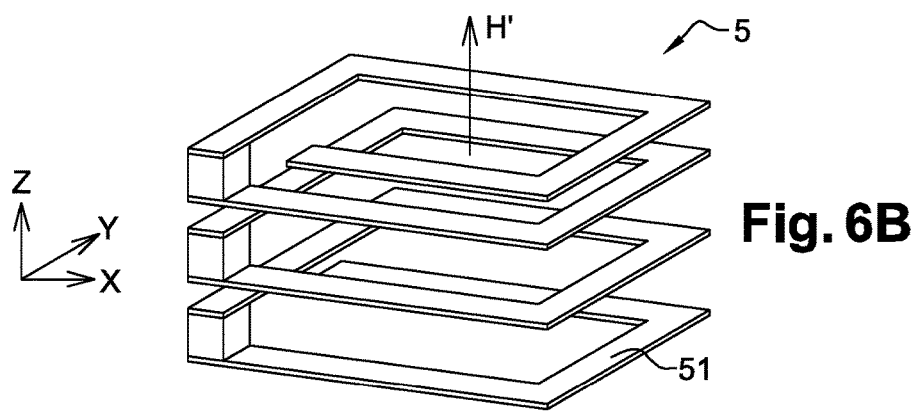
FIG. 6B is a schematic exploded perspective view of a micro-coil as excitation device according to another embodiment.

In another embodiment, and as illustrated in FIG. 6b, the excitation device 5 can be a three-dimensions micro-coil 51 manufactured with alternating conductive and isolating layers such as the interconnect layers of an Integrated Circuit manufacturing process (MEMS, CMOS, BiCMOS, or any similar type of IC process).

With this arrangement, an ultra-low power operation of the miniature atomic clock integrating such apparatus can be achieved as the current in the excitation device is minimum and the ESR signal strength is maximized due to the orthogonality between the exciting magnetic field and the static magnetic field over the volume occupied by the medium.

Detection Device

The detection of the spin resonance via the monitoring of the excitation device can be performed in multiple different manners. Without restricting the methods to perform detection of resonance, two examples on how to proceed to the detection of the resonance are provided below.

In a first solution, the magnetic permeability of the medium located above the excitation device is affected at resonance of the medium. This modification of the magnetic permeability of the medium at resonance affects the electrical impedance of the excitation device. This change of electrical impedance can then be detected or measured with appropriate circuitry and fed back to the excitation device to lock the excitation frequency to the resonant frequency of the medium. In practice, there are multiple circuits capable of detecting a change of impedance of a device. For instance, a change of electrical impedance may translate into a change of the current going through a component, or a change of the voltage across a component, or even the modification of the transparency of a specific medium.

In a second solution, the magnetic flux through the excitation device 5 changes abruptly at resonance. Such variation of flux creates an electro-motive force in the detection device and an additional current appears in the detection device. This change of current intensity can then be detected or measured with appropriate circuitry and fed back to the excitation device to lock the frequency of the excitation to the resonant frequency of the medium. In practice, a change of current may be detected in multiple manners, using active components and circuitry or simple passive components like the change of voltage across a resistor.

Frequency Generator

The frequency generator is notably used to scan the excitation frequency (or the plurality of excitation frequencies) of the excitation device until the electron spin resonance of the medium is detected by the detection device. Once the spin resonance is detected, the frequency generator is driven and locked in order to stabilize the excitation frequency of the excitation device at the frequency at which the spin resonance has been detected. For example, the frequency generator can be a Voltage Controlled Oscillator coupled to the excitation device.

Frequency-Lock Device

The frequency-lock device is used to lock the excitation frequency to the frequency of the detected spin resonance. For example, the frequency-lock device can be a Phase Lock Loop that drives the frequency generator according to the output of the detection device. As the medium has very well determined electronic transitions, the output of the Phase Lock Loop is also very well defined and by consequence so is the excitation frequency.

ESR Signal Strength Optimization

In a particular configuration in which the static magnetic field B is quasi-in-plane within the full volume occupied by the medium, and in which the excitation device is also in-plane, the ESR signal strength is maximized as the excitation magnetic field H is perpendicular to the static magnetic field.

This configuration makes the described embodiments extremely robust from a manufacturing process standpoint and does not need to establish a predominant direction of the spin of the particles of the medium. The property of orthogonality of the two magnetic fields makes the device not sensitive to the relative positioning of the different elements which constitute the atomic clock.

As an example, any angular inaccuracy rising from the misalignments during the bonding of the second substrate with the first substrate does not influence the ESR signal strength.

Improvement of Signal to Noise Ratio

In order to improve the signal to noise ratio, it is possible to introduce small amplitude magnetic field modulation. In other words, an oscillating magnetic field is super-imposed on the static magnetic field B by means of micro-coils.

Operation of the miniature atomic clock is then slightly modified to account for this improvement and is described below.

Because of this additional small signal modulation, when the excitation magnetic field H is in the vicinity of the resonance line of the medium, it is swept back and forth through part of the line, leading to an alternating (AC) signal in the detection device. One method then consists to amplify this AC component of the signal using a frequency selective amplifier, thus eliminating a great deal of noise. The modulation amplitude is normally less than the linewidth of the resonant curve of the medium so that the AC signal obtained is proportional to the change of the medium state.

For example, the micro-coils used as oscillating magnetic device are built with alternating layers of conductive and isolating materials, and are preferably placed in the thickness of the second substrate as illustrated in FIG. 4. The micro-coils 7a and 7b are driven in phase by the modulating current and generate an in-plane modulation of the static magnetic field within the volume of the medium.

Reducing the Sensitivity to External Environment

External environment may affect the operation of the miniature atomic clock. In particular, an additional static (DC) magnetic field from the operating environment may disturb the medium and produce modification of the energy difference between the spin levels of the medium, which in turns produces a frequency shift of the output signal of the miniature atomic clock. AC magnetic fields may also produce similar unwanted effects on the stability and accuracy of the output signal of the clock. In order to improve the robustness and the stability of output of the miniature atomic clock, it is possible to include an electromagnetic shield encapsulating some elements of the apparatus.

Figure 7:
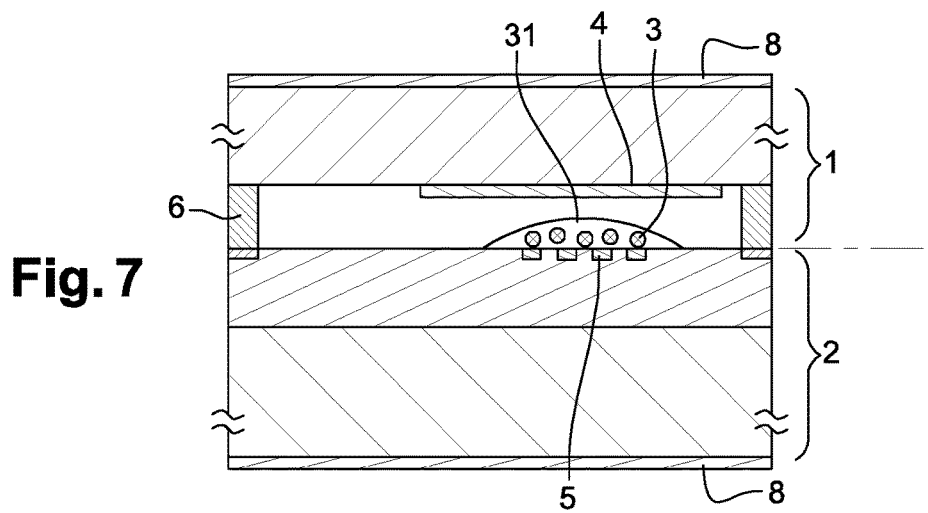
FIG. 7 is a schematic cross-section view of the apparatus equipped with an electromagnetic shield.

The electromagnetic shield 8 may continuously surround the apparatus as illustrated in FIG. 7. High magnetic permeability materials are used to guide the external magnetic fields away from the volume occupied by the medium. Without restriction to these materials to provide the requested shield, suitable material typically include alloys made of nickel, iron, molybdenum or chromium, and copper.

The electromagnetic shield can be formed around the stack of first and second substrates using an additional level of packaging for the atomic clock. The electromagnetic shield may discontinuously surround the apparatus. The electromagnetic shield may partially protect the apparatus. The electromagnetic shield may be integrated within the first substrate and/or within the second substrate.

Optional Layers

As illustrated in FIGS. 1 and 2, an optional separation layer acting as an isolating layer 30 may be disposed between the medium and the excitation device. The role of such layer is mainly to avoid any potential short-circuit or electronics malfunctioning of the excitation device which the direct contact of the medium with the excitation device may cause.

In practice, the isolating layer 30 should preferably comprise micro-structuration or nano-structuration. Such structuration may be used to create sites in which the endohedral fullerenes can preferably be located. As an example, appropriate location of the particles enables finer linewidth of the energetic transitions by increasing the distance between the spins of the different particles. As another example, appropriate location of the particles enables better control of the linewidth of the energetic transitions and reproducibility of the device in an industrial process. The interactions between endohedral fullerenes and their influence on the quality of the output of the atomic clock are described in section "Interactions Between Endohedral Fullerenes" of document U.S. Pat. No. 7,142,066 B1.

Another optional cover layer 31 may be disposed on top of the medium to maintain the medium in place.

Configuration with Out-Of-Plane Static Magnetic Field and In-Plane Excitation Magnetic Field In this configuration, the static magnetic field B is quasi-perpendicular to the planar surfaces of the substrates, and the excitation magnetic field H is generated parallel to the planar surfaces in order to maintain the orthogonality between the two magnetic fields within the volume occupied by the medium. The excitation and detection devices may be used in a similar way than described above to detect the spin resonance. One may use an in-plane modulation device to perform the modulation of the static out-of-plane magnetic field. For instance, this configuration can be realized in a similar manner than in FIG. 4 with this time: out-of-plane magnetization of the permanent magnets on the first substrate using an optional in-plane micro-coil as the oscillating magnetic device, and one or more micro-coils as the excitation device.

Other Location of the Medium

Figure 8:
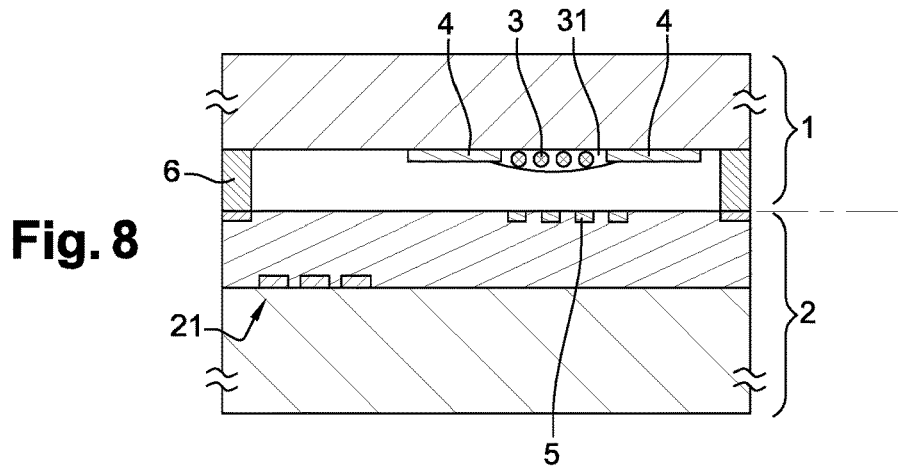
FIG. 8 is a schematic cross-section view of the apparatus according to another embodiment wherein the medium is located on the magnetic substrate.

As illustrated in FIG. 8, the medium 3 can be located on the first substrate 1 together with the magnetic device 4. The considerations recited above regarding the homogeneity of the static magnetic field produced in the volume of the medium should be obtained.

Stabilization of the Operating Temperature

The frequency at which electron spin resonance of the medium occur may depend on temperature. The hyperfine transitions of the medium may be affected by the temperature. For example, whenever endohedral fullerenes are used, temperature variation causes some stress on the species captured inside the "cage" of Carbon. This stress affects the energy levels of the spins of the medium and may create some temperature-depend output signal. In practice, one may achieve stable temperature in multiple ways like heating the device locally (with a current passing through a resistor for instance) either in open loop or closed loop configuration.

Operating Method

Figure 12:
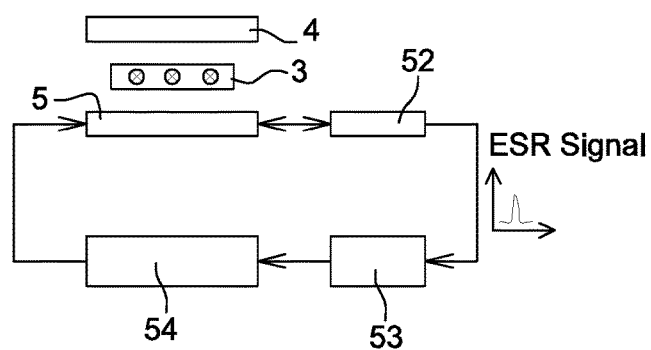
FIG. 12 is a block diagram showing the link of part of the devices integrated in the apparatus according to an embodiment with part of the electrical circuit such as the frequency generator, the detector and the lock device.

The general operation mode of the apparatus according to the particular embodiment illustrated in FIG. 12 may comprise:

a first phase of operation consisting in the ignition of the apparatus, and a second phase of operation where the output signal of the apparatus itself is used to stabilize the excitation frequency (or frequencies).

The first phase of operation consists on the search of the excitation frequency (or frequencies) at which the spin resonance of the medium occurs. It may consist in sweeping the excitation frequency of the excitation device 4 within a predetermined range of frequencies via the frequency generator 54, and monitoring an electrical characteristic of the excitation device 4 by the detection device 52 until the spin resonance is detected.

In other words, the excitation frequency (or frequencies) is scanned to search the optimal excitation frequency (or frequencies) for the excitation device, until the electron spin resonance of the medium is detected by the detection device. Depending on the design of the various elements composing the clock, one may use a low stability tunable frequency generator to initiate the resonance.

The research phase may be achieved by sweeping the voltage across a Voltage Controlled Oscillator (with a ramp for instance) so that the excitation frequency is tuned until Electron Spin Resonance of the medium occurs. There are multiple other implementations of devices capable of performing this first research phase, including without limitation, ring oscillators or digital frequency synthesizers, or even quartz oscillators.

In practice, if multiple excitation frequencies are necessary to excite the medium, one may use multiple oscillators or a single oscillator with multiple frequency dividers or a combination of these.

In practice, the second stage of ignition may be achieved by locking the excitation frequency by feeding back the output signal of the detection device to the frequency generator. Thus, when the detection device 52 detects that a spin resonance occurs, it sends an output signal to the frequency-lock device 53, for example a Phase Lock Loop (PLL), to drive the frequency generator 54 so as to lock the excitation frequency to the frequency at which the spin resonance has occurred. As the medium has very well determined electronic transitions, the output of the Phase Lock Loop is also very well defined and by consequence so is the excitation frequency. In such closed loop configuration, the excitation frequency that is necessary to excite the medium is generated by the medium itself which enables ultra-stable excitation of the medium at the Electron Spin Resonance frequency and therefore stable operation of the clock.

In such configuration, any frequency (and its multiples and its sub-multiples) generated in the loop, including the frequency of the electron spin resonance, can be used as an output signal to be used as a time-keeping reference.

The Manufacturing Process Suitable for a Particular Embodiment

Briefly, the manufacturing method comprises:
forming the magnetic substrate by adequately arranging the magnetic device to the first substrate;
forming the reference substrate by adequately arranging the excitation device in the second substrate having at least a planar surface;
forming the medium; and
sealing the magnetic substrate to the reference substrate so that the static magnetic field created by the magnetic device and the excitation magnetic field created by the excitation device are orthogonal to each other.

The magnetic device can be simply affixed to the first substrate by any traditional methods, or can be a portion of the first substrate. For example, one can use magnetic transfer techniques or semiconductor compatible technologies (for example sputtering, electroplating) or one can glue or solder permanent magnets, or any method which enables the manufacturing of permanent magnets on a substrate.

Of course, any other electrical circuits, such as the detection device, the frequency generator, the frequency-lock device, and the device for stabilizing the temperature of the volume in which the medium is located at a substantially constant temperature, can also be arranged in the second substrate before the sealing.

FIGS. 9A to 9D schematically show a sequence of semiconductor-like processing steps suitable for fabricating the magnetic substrate.

Figure 9A:
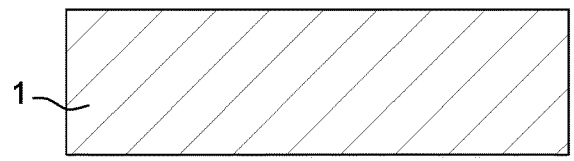
FIGS. 9A to 9E schematically show processing steps for making a magnetic substrate according to an embodiment.
Figure 9B:
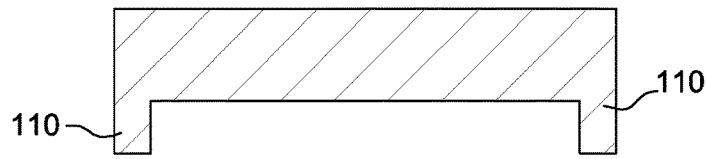
Figure 9C:
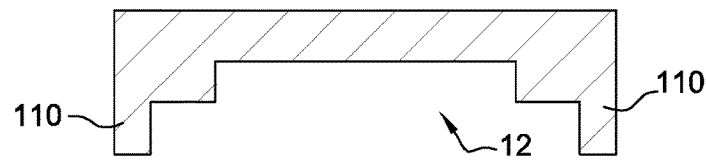
Figure 9D:
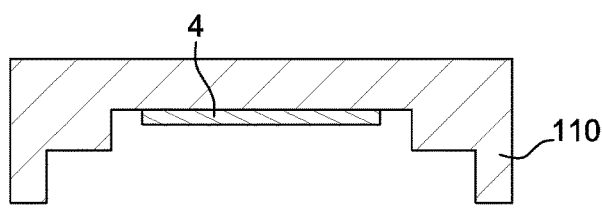
Figure 9E:
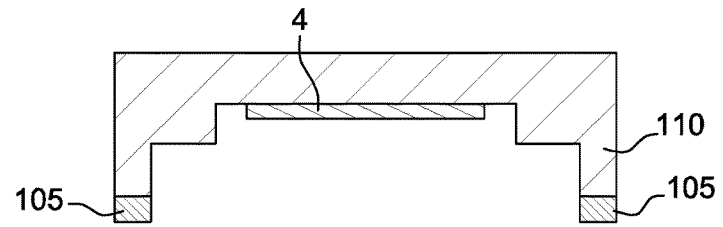

The first substrate 1 is preferably a Silicon or Glass wafer (FIG. 9A).

After cleaning, optional stand-offs 110 are formed (FIG. 9B) by lithographic patterning followed by an etch. On Silicon wafers, a KOH etch is suitable for this steps but it exists multiple technical solution to perform this etch. The purpose of the stand-offs 110 is to precisely determine the vertical separation between the magnetic substrate 1 and the reference substrate 2, as well as to enhance the reproducibility of the assembly process of the two substrates.

Lithographic patterning is used to etch an optional cavity 12 (FIG. 9C) within the first substrate 1. The purpose of this cavity 12 is to increase the distance between the magnetic device layers and the medium in such a way that the static magnetic field generated by the magnetic device is homogeneous within the volume occupied by the medium after assembly of the first substrate and the second substrate.

At least one layer of magnetic material is then deposited to form the magnet device 4 (FIG. 9D) in the cavity of the first substrate 1. Without limiting the techniques which could be used to create such magnetic device 4, sputtering through a shadow mask is suitable for the realization of this step. The first substrate 1 may be annealed in the presence or not of a magnetic field to further improve the properties of the magnetic device 4.

A patterned layer 105 is then formed or deposited on the first substrate 1. Preferably, the patterned layer 105 is a Geranium (Ge) based layer which is deposited and then patterned. However, other materials and other techniques like screen printing could also be used to realize the same. The patterned layer may also be organic material like resist, polymer, glu, or any other compatible material.

For a better control of the various thicknesses of the layers, one may use an SOI (Silicon On Insulator) or a double SOI wafer as the starting material and adapt the manufacturing process to do the same.

Figure 10A:
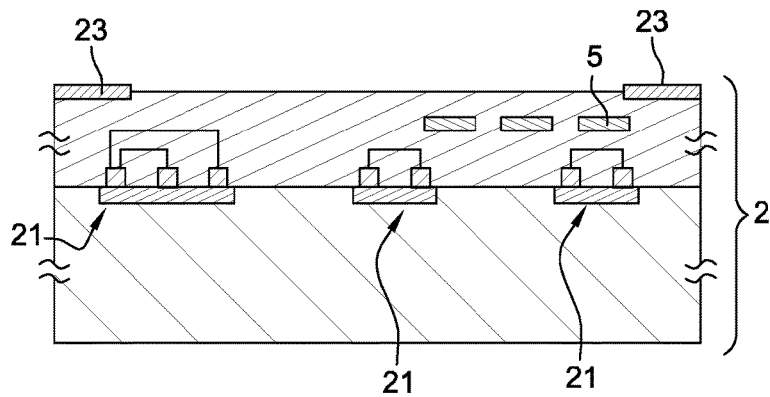
FIGS. 10A and 10B schematically show processing steps for making a reference substrate according to an embodiment.
Figure 10B:
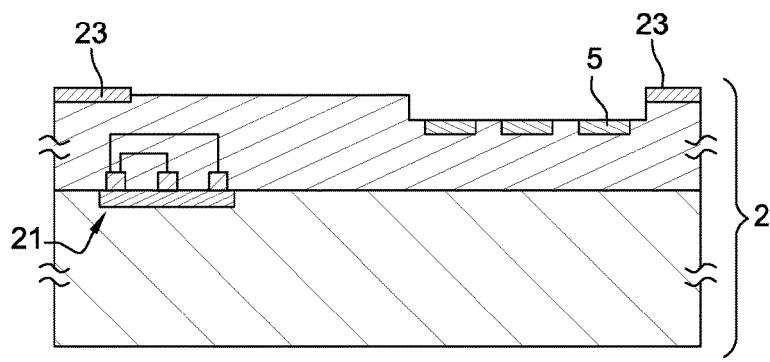

As for the reference substrate, FIGS. 10A and 10B schematically show a sequence of processing steps suitable for fabricating the reference substrate 200.

The second substrate 2 is preferably a chip made with conventional SOI or Silicon adapted for (Bi)CMOS circuitry/technology in which active areas 21 are defined and excitation and detection devices are integrated (FIG. 10A). The active areas 21 may comprise regions that will make mechanical and/or electrical contact with the magnetic substrate 1, as well as circuitry for driving the excitation device, and circuitry for sensing output signals from the detection device. A layer metal layer 23 can also be deposited according to conventional (Bi)CMOS process. Such metal layer 23 is notably a metal suitable for use as bond metal and/or bond pads. In addition, any layer(s) of metal of the second substrate 2 may define the excitation device 5. As an option, a recess 22 can then be etched in the insulating layer of the second substrate between interconnect metallic layers (FIG. 10B).

The medium 3 can then be fixed to the reference substrate 2 (not shown) above the excitation device 5.

Figure 11A:
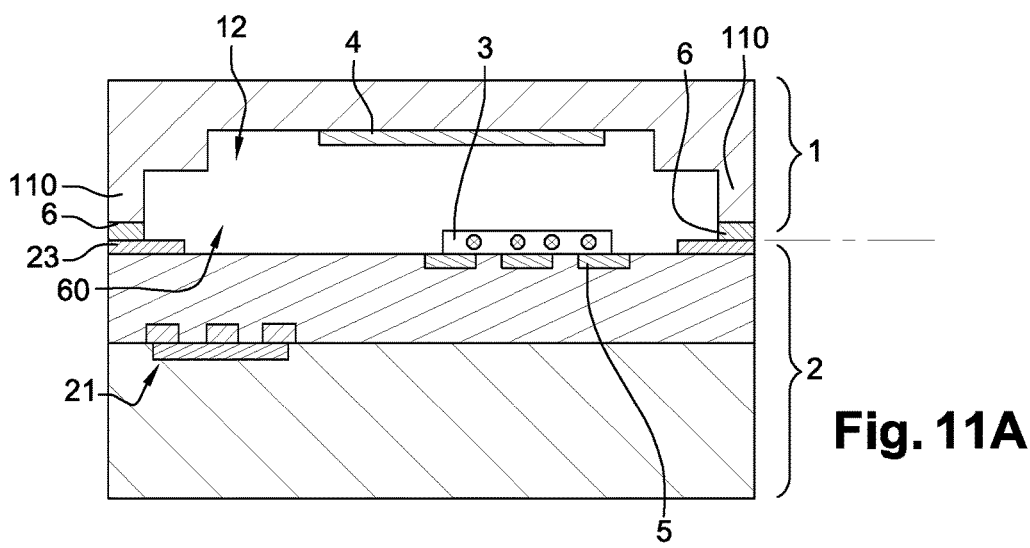
FIGS. 11A and 11B schematically show processing steps for making an assembly of magnetic substrate and reference substrate according to an embodiment.
Figure 11B:
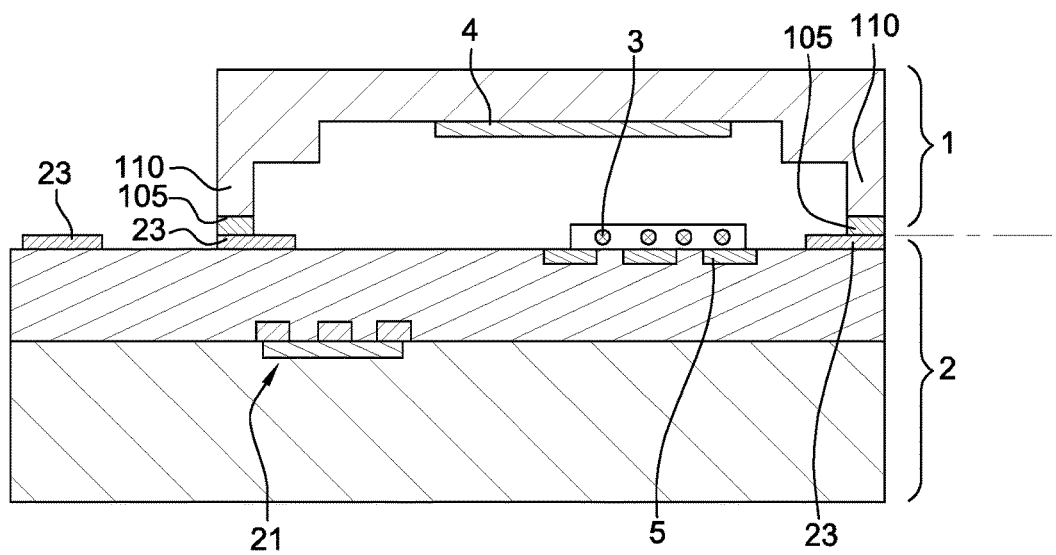

The final assembly of the magnetic substrate 1 with the reference substrate 2 is illustrated in FIGS. 11A to 11B. The reference substrate 2 illustrated in FIGS. 11A and 11B is exempt from recess 22.

On FIG. 11A, the reference substrate 2 is attached to the magnetic substrate 1 via an aligned metal to metal bond between patterned layer 105 as the mechanical connection 6 on the magnetic substrate 1, and metal layer 23 as bond pads on the reference substrate 2. The bonding of the reference substrate 2 to the magnetic substrate 1 occurs at a later stage of processing than the manufacturing of the reference substrate 2. Accordingly, relatively low temperature bonding processes are preferred for bonding the reference substrate 2 to the magnetic substrate 1, including but not limited to: eutectic metal bonding, aluminum-Germanium bonding, solder bonding, Indium-Gold bonding, Gold-Silicon bonding, Glass frit bonding, any adhesive wafer bonding and polymer bonding.

The separation between the medium 3 and the magnetic device 4 is determined by the combined thickness of stand-offs 110, patterned layer 105, cavity depth in the magnetic substrate, thickness of the magnetic device and recess depth in the magnetic substrate 1. Although the processing sequence in FIG. 6A shows standoffs 110 on magnetic substrate 1, it is also possible to form standoffs on the reference substrate 2, or on both magnetic and reference substrates 1, 2 in order to define the separation between the medium 3 and the magnetic device 4.

The reference substrate 2 is preferably attached to the magnetic substrate 1 via a metal-to-metal bond, which can be made hermetic. As a result, the entire assembly of the reference substrate 2 and the magnetic substrate 1 can provide hermetic barrier between the elements of the atomic clock and an ambient environment.

In order to further increase immunity to ambient environment, the assembly of substrates can be coated on both sides or on one single side by at least one layer of mu-metal in order to shield the elements of the atomic clock from external Electro-Magnetic Environment.

Further, as illustrated in FIG. 6B, material can be etched away from the magnetic substrate to allow access to some active area from above via the interconnect layer of the reference substrate 2. By allowing access to active areas 21 from above, electrical connection to the atomic clock is facilitated.

Other configurations of the magnetic and/or reference substrate includes the use of Through Silicon Vias (TSV) in any or both the substrates to allow electrical access to some active area(s) from above or from below.

The solution described above allows producing a quasi-uniform magnetic field intensity over a certain medium by using a structure of permanent magnet and exciting the medium via a structure of micro-coil instead of a resonant circuitry. Another advantage of the present solution is that the detection is achieved by monitoring one of the characteristics of the structure of micro-coil itself, such as the variation of the impedance, instead of a resonant cavity.

The invention claimed is:

1. Apparatus for atomic clock comprising:
   first and second distinctive substrates, each having at least a planar surface substantially parallel therebetween;
   a medium having particles capable of undergoing energetic transition between at least two energy levels, said medium being located in the space defined between said planar surfaces;
   a magnetic device arranged to the planar surface of the first substrate and generating at least in the volume of the medium a predetermined static magnetic field B the direction of which is substantially parallel to a reference plane parallel or perpendicular to the planar surfaces;
   an excitation device arranged to the second substrate and facing the medium, said excitation device generating an excitation magnetic field H at, at least an excitation frequency, the direction of said excitation magnetic field H in the volume of the medium being substantially orthogonal to said direction of the static magnetic field B.

2. Apparatus according to claim 1, wherein it further comprises:
   a frequency generator generating a tunable frequency, said excitation frequency being based on said tunable frequency;
   a detection device detecting the occurrence of a spin resonance of the medium by monitoring a signal representative of the influence of the energetic transition of the particles over the excitation device; and
   a frequency-lock device locking the generated tunable frequency to the frequency at which the spin resonance has occurred.

3. Apparatus according to claim 1, wherein the magnetic device is a structure of permanent magnet formed with a single permanent magnet or a plurality of distinctive permanent magnets.

4. Apparatus according to claim 1, wherein the magnetic device is a structure of permanent magnet formed in a portion of the first substrate.

5. Apparatus according to claim 1, wherein the magnetic device is located on the planar surface of the first substrate.

6. Apparatus according to claim 1, wherein the magnetic device is located in a recess of the first substrate.

7. Apparatus according to claim 1, wherein the excitation device is formed with a structure of planar micro-coil having at least a spiral planar micro-coil or at least a spiral multi-layers micro-coil.

8. Apparatus according to claim 1, wherein the excitation device is integrated in the thickness of the second substrate.

9. Apparatus according to claim 7, wherein the detection device further comprises a module detecting a variation of the electrical impedance of the structure of planar micro-coil for detecting the occurrence of a spin resonance of the medium.

10. Apparatus according to claim 7, wherein the detection device further comprises a module detecting a variation of the current intensity of the structure of planar micro-coil for detecting the occurrence of a spin resonance of the medium.

11. Apparatus according to claim 7, wherein the detection device further comprises a module detecting a variation of the voltage value between the ports of the planar micro-coil for detecting the occurrence of a spin resonance of the medium.

12. Apparatus according to claim 1, wherein it further comprises an oscillating magnetic device generating an oscillating magnetic field H' substantially parallel to the static magnetic field B.

13. Apparatus according to claim 1, wherein it further comprises an isolating layer between the medium and the excitation device.

14. Apparatus according to claim 1, wherein it is covered by a patterned metal electro-magnetic shield to reduce the sensitivity of the apparatus to external environment.

15. Apparatus according to claim 1, wherein it further comprises device for maintaining the volume in which the medium is located, at a substantially constant temperature.

16. Method for manufacturing the apparatus for atomic clock, comprising:
forming a magnetic device arranged to a first substrate having at least a planar surface, the magnetic device generating a predetermined static magnetic field B the direction of which is substantially parallel to a reference plane parallel or perpendicular to the planar surface of the first substrate;
forming at least an excitation device in a second substrate having at least a planar surface, said excitation device generating an excitation magnetic field H at, at least, an excitation frequency, the excitation magnetic field having a direction substantially orthogonal to said reference plane;
forming a medium having particles capable of undergoing energetic transition between at least two energy levels, on one of the first and second substrates;
sealing the first substrate to the second substrate so that their respective planar surfaces are facing each other and substantially parallel therebetween, and so that the medium is located in the space defined between said planar surfaces.

17. Method for operating an apparatus for atomic clock, having at least: (i) first and second distinctive substrates, each having at least a planar surface substantially parallel therebetween, (ii) a medium having particles capable of undergoing energetic transition between at least two energy levels, said medium being located in the space defined between said planar surfaces, (iii) a magnetic device arranged to the planar surface of the first substrate and generating at least in the volume of the medium a predetermined static magnetic field B the direction of which is substantially parallel to a reference plane parallel or perpendicular to the planar surfaces, (iv) an excitation device arranged to the second substrate and facing the medium, said excitation device generating an excitation magnetic field H at, at least an excitation frequency, the direction of said excitation magnetic field H in the volume of the medium being substantially orthogonal to said direction of the static magnetic field B, the operating method comprising:
simultaneously driving a frequency generator to sweep a tunable frequency applied to the excitation device within a predetermined range of frequencies, and monitoring the excitation device to detect the occurrence of a spin resonance in the medium;
when a spin resonance is detected, driving the frequency generator to lock said tunable frequency to the frequency at which the spin resonance has occurs;
setting the excitation frequency to said locked tunable frequency.

18. The manufacturing method according to claim 16, wherein it further comprises, before the sealing of the first substrate to the second substrate:
coupling a detection device to the excitation device, the detection device detecting the occurrence of a spin resonance of the medium by monitoring a signal representative of the influence of the energetic transition of the particles over the excitation device;
coupling a frequency generator to the excitation device, the frequency generator generating a tunable frequency on which the excitation frequency is based; and
coupling a frequency-lock device to the detection device and to the frequency generator, the frequency-lock device locking the generated tunable frequency to the frequency at which the spin resonance has occurred.

19. The operating method according to claim 18, wherein it further comprises stabilizing the temperature of the volume in which the medium is located at a substantially constant temperature.

* * * * *